US009329110B2

(12) United States Patent
Krebs (10) Patent No.: US 9,329,110 B2
(45) Date of Patent: May 3, 2016

(54) APPARATUS FOR DISTRIBUTING FLUID TO A PLURALITY OF SAMPLE CONTAINERS

(71) Applicant: PIETER VAN WEENEN & CO. GmbH, The House of Innovation, Waldkirch (DE)

(72) Inventor: Tobias Krebs, Gutach (DE)

(73) Assignee: PIETER VAN WEENEN & CO. GmbH, The House of Innovation, Waldkirch (DE)

( * ) Notice: Subject to any disclaimer, the term of this patent is extended or adjusted under 35 U.S.C. 154(b) by 470 days.

(21) Appl. No.: 13/681,562

(22) Filed: Nov. 20, 2012

(65) Prior Publication Data

US 2013/0174672 A1    Jul. 11, 2013

(30) Foreign Application Priority Data

Nov. 20, 2011    (DE) .......................... 10 2011 118 958

(51) Int. Cl.

| *G01N 1/38* | (2006.01) |
|---|---|
| *G01N 1/00* | (2006.01) |
| *C12M 3/00* | (2006.01) |
| *C12M 1/00* | (2006.01) |
| *C12M 1/34* | (2006.01) |

(52) U.S. Cl.
CPC ................ *G01N 1/38* (2013.01); *C12M 23/44* (2013.01); *C12M 23/58* (2013.01); *C12M 29/00* (2013.01); *C12M 41/34* (2013.01); *G01N 1/00* (2013.01)

(58) Field of Classification Search
None
See application file for complete search history.

(56) References Cited

U.S. PATENT DOCUMENTS

| 3,582,284 A | * | 6/1971 | Hamshere et al. ............. 422/535 |
| 3,766,016 A | * | 10/1973 | Guigan ...................... 435/309.1 |
| 3,901,653 A | * | 8/1975 | Jones et al. ..................... 222/71 |

(Continued)

FOREIGN PATENT DOCUMENTS

| CN | 202478894 U | * | 10/2012 | ................ B01J 4/00 |
| DE | 2055304 |   | 5/1971 | |

(Continued)

OTHER PUBLICATIONS

First Office Action issued on Jun. 11, 2012 for priority application No. DE 10 2011 118 958.4. (in German).

*Primary Examiner* — Paul West
(74) *Attorney, Agent, or Firm* — Miller, Matthias & Hull LLP (57) ABSTRACT

The present disclosure relates to a distribution apparatus for a sample exposition arrangement comprising at least two sample containers and a fluid source for fluid to be supplied to the sample containers. The distribution apparatus includes a distribution device including a distribution device inlet for supplying fluid to the distribution device, one distribution device outlet each per sample container, and a distribution chamber between the distribution device inlet and the distribution device outlets. The distribution apparatus further includes at least one fluid outlet device per distribution device outlet. The at least one fluid outlet device includes one fluid-outlet device inlet in fluid communication with the corresponding distribution device outlet, a first fluid-outlet device outlet for discharging fluid into the corresponding sample container, and a second fluid-outlet device outlet for discharging excess fluid. The present disclosure also relates and to a sample exposition arrangement that includes the distribution apparatus.

16 Claims, 11 Drawing Sheets

(56) References Cited

U.S. PATENT DOCUMENTS

| | | | |
|---|---|---|---|
| 4,283,497 A * | 8/1981 | Hirshaut | C12M 29/00 |
| 5,175,086 A * | 12/1992 | Takekawa et al. | 435/7.92 |
| 5,609,828 A | 3/1997 | O'Bear et al. | |
| 8,993,314 B2 * | 3/2015 | Eckelberry et al. | C12M 1/04 |
| 2002/0059945 A1 * | 5/2002 | Maiefski | B01J 19/0046 134/25.1 |
| 2009/0275115 A1 | 11/2009 | Jury et al. | |
| 2010/0112681 A1 * | 5/2010 | Asogawa et al. | G01N 33/50 |

FOREIGN PATENT DOCUMENTS

| | | |
|---|---|---|
| JP | 2005-345186 | 12/2005 |
| JP | 2007-075051 | 3/2007 |

* cited by examiner

APPARATUS FOR DISTRIBUTING FLUID TO A PLURALITY OF SAMPLE CONTAINERS

CROSS-REFERENCE TO RELATED APPLICATIONS

This application claims priority under 35 USC §119 and the Paris Convention to German Application No. DE 10 2011 118 958.4, filed on Nov. 20, 2011.

FIELD OF THE DISCLOSURE

The present disclosure generally relates to apparatuses for exposing a sample to an air-borne mixture.

FIELD OF THE DISCLOSURE

Gassing apparatuses, also referred to as culture or exposition apparatuses, are used to charge a sample (e.g. cell or bacteria culture, chemical testing substance) with a fluid and to examine what effect the fluid has on the sample.

Possible fluids are, for example, gases, gas mixtures, air-borne substances, air-borne mixtures (e.g. smoke of tobacco products, such as cigarettes and cigars), aerosols, environmental pollutants, medical substances, exhaust gases, such as e.g. combustion exhaust gases, air-borne particles, etc.

Usually a number of sample containers including one sample each are provided in a gassing apparatus, which containers are supplied with a fluid from a common fluid source. For example, a device generating the fluid (e.g. smoke machine, aerosol generator, engine test bed, feed systems, such as e.g. feed pumps for air, etc.) or a storage device for the fluid (e.g. gas bottles, fluid collecting containers) may be used as a source.

The fluid to be supplied to the samples may, in part, be initially diluted (e.g. with ambient air, oxygen, synthesized air, pressured air, etc.) and/or enriched with one or more further fluids (e.g. pollutants) prior to being supplied to the sample containers.

When using a common fluid source, a distribution apparatus between the fluid source and the sample containers is in general required.

The present disclosure provides solutions enabling a distribution of fluid to be supplied to a plurality of sample containers which is improved over known approaches.

BRIEF DESCRIPTION OF THE DISCLOSURE

The present disclosure provides a distribution apparatus and a sample exposition arrangement according to the independent claims. Preferred embodiments are defined in the dependent claims.

In particular, the present disclosure provides a distribution apparatus for a sample exposition arrangement having at least two sample containers and a fluid source for fluid to be supplied to the sample containers. The distribution apparatus according to the disclosure comprises a distribution device including a distribution device inlet for supplying fluid to the distribution device. The distribution device inlet can be connected, for example, to a fluid inlet of the distribution device inlet or be in fluid communication therewith. The distribution device further comprises one distribution device outlet each per sample container, and a distribution chamber between the distribution device inlet and the distribution device outlets. The distribution apparatus further comprises at least one fluid outlet device per distribution device outlet. The at least one fluid outlet device comprises one fluid-outlet device inlet each which is in fluid communication with the corresponding distribution device outlet, a first fluid-outlet device outlet for discharging fluid into the corresponding sample container, and a second fluid-outlet device outlet for discharging excess fluid.

The distribution device can comprise at least one fluid guideway each between the distribution chamber and the distribution device outlets.

The distribution chamber can be substantially spherical or hemispherical in shape.

A device having an effect on flow can be arranged within the distribution chamber.

A fluid guiding recess for each fluid guideway can be formed in the inner surface of the distribution chamber.

The distribution device can comprise a removable cover defining at least one part of the distribution chamber.

The distribution chamber, at least in part, and/or the fluid guideways can be formed within a first body of the distribution device.

The fluid guideways can, at least in part, be formed within a second body.

The first body and the second body can be provided as separate components which may be connected.

The first body and the second body can each comprise complementary recesses forming the fluid guideways.

The fluid guideways may be substantially equal in dimension and/or at least one of the fluid guideways can be curved.

The fluid-outlet device outlets can be in fluid communication with an excess fluid container for discharging excess fluid.

The excess fluid container can comprise an outlet for discharging fluid present therein.

The distribution apparatus can comprise a fluid supply selection device which is in fluid communication with the second fluid-outlet device outlets and the distribution device inlet and which is adapted to supply either fluid from the fluid source or fluid from the second fluid-outlet device outlets or a mixture of fluid from the fluid source and fluid from the second fluid-outlet device outlets to the distribution device inlet.

The distribution apparatus can comprise a fluid volume compensation device which is in fluid communication with the second fluid-outlet device outlets.

Furthermore, the present disclosure provides a sample exposition arrangement comprising a distribution apparatus according to the disclosure.

The sample exposition arrangement can comprise at least two sample containers and/or a fluid source for fluid to be supplied to the sample containers.

BRIEF DESCRIPTION OF THE DRAWINGS

Preferred embodiments of the present disclosure are described in the following with reference to the attached drawings; in which.

DETAILED DESCRIPTION OF THE DISCLOSURE

Figure 1:
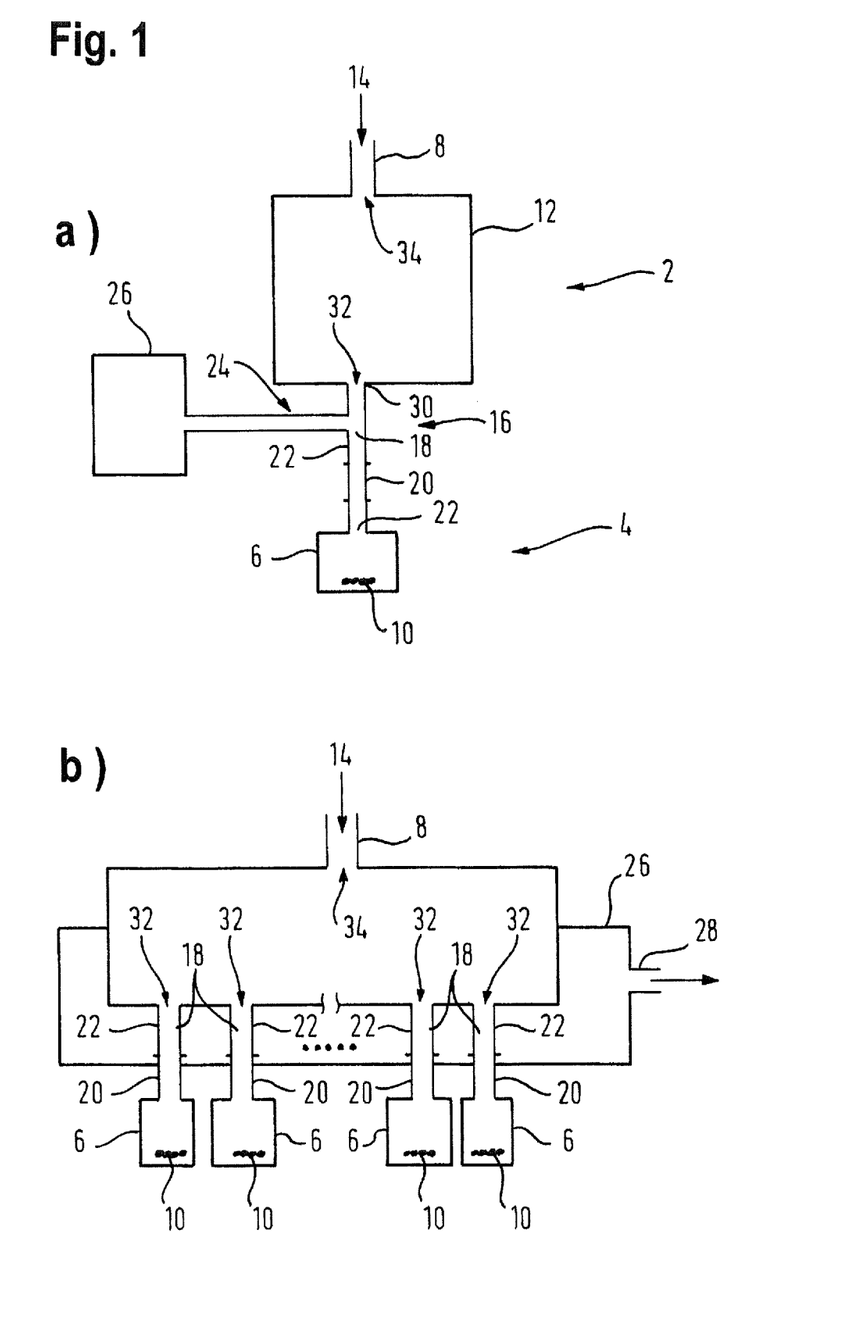
FIG. 1 shows a schematic illustration of a sample exposition arrangement including a distribution apparatus and a sample container arrangement.

FIG. 1 shows a sample exposition arrangement comprising a distribution apparatus, designated by 2 as a whole, and an arrangement 4 including sample containers 6. During operation of the sample exposition arrangement, fluid (e.g. an airborne mixture), which is provided by a fluid source, is supplied to the distribution apparatus 2 via a fluid inlet 8, is distributed by means of the distribution apparatus 2 and supplied to the sample containers 6 and samples 10 disposed therein.

The distribution apparatus 2 comprises a distribution device 12 which can be supplied with fluid on the inlet side via the fluid inlet 8, which is illustrated by arrow 14. The fluid inlet 8 can be adapted in cross section to a fluid supply line from the fluid source by means of, for example, one or more adapter sleeves, adapters or such like. In the distribution device 12, supplied fluid is distributed and supplied to fluid outlet devices 16, as explained in greater detail in the following.

Fluid can be introduced into the sample containers 6 via first fluid-outlet device outlets 18 of the fluid outlet devices 16. For this purpose, the first fluid-outlet device outlets 18 can be connected to the inlets 22 of the sample containers 6, for example, by means of tube or pipe connections 20, or can be fitted directly to the inlet pipes leading to the sample containers.

The number of fluid outlet devices 16 corresponds to the shown number of sample containers 6 and can be substantially freely chosen, as indicated in FIG. 1 (b) by the dots between the fluid outlet devices 16, just as the number of sample containers 6. For example, embodiments having two, three, four, etc. fluid outlet devices 16 and sample containers 6 are provided which are arranged in a row as in the shown embodiment. In further embodiments, a plurality of two and more fluid outlet devices 16 and sample containers 6, respectively, arranged side by side in a row can be used. Furthermore, more than one fluid outlet device 16 can be provided per sample container 6. It is also possible to supply more than one sample container 6 by one fluid outlet device 16.

The fluid outlet devices 16 further comprise second fluid-outlet device outlets 24, via which fluid may also be discharged, however, not to the sample containers 6. Rather, fluid which is not to be and/or cannot be supplied to the sample containers 6 is discharged via the second fluid-outlet device outlets 24.

Such a fluid, which is also referred to as fluid excess or excess fluid in the following, can occur when, for example, the amount of fluid supplied to the distribution apparatus 2 is higher than the amount of fluid required for exposition of the samples 10. For example, it is possible that the distribution apparatus 2 is supplied with approximately three liters of fluid per minute, however, the sample containers 6 are each supplied with only approximately 5 milliliters per minute (i.e. a total of 15 milliliters per minute in the case of 3 sample containers). This may, for example, be due to the fact that fluid is drawn into the sample containers 6 which controls the supply of fluid and also limits the same.

One advantage of removing fluid excess just ahead of the sample containers 6 is that the fluid (and thus the constituents thereof, e.g. particles) to be supplied to the sample containers 6 can be transported over a considerably longer time than in known approaches and at a higher speed until the end (i.e. substantially up to directly ahead of the sample containers 6). This results in lower losses which may occur when the fluid (and thus the constituents thereof, e.g. particles) is transported over a greater distance at a lower flow rate (e.g. 5 milliliters per minute).

In such cases, excess fluid is removed via the second fluid-outlet device outlets 24 and can be supplied to an optional excess fluid container 26. The excess fluid container 26 itself can be used to collect excess fluid (at least in part) and/or can be connected to a separate collection device (e.g. for later disposal) via an excess fluid container outlet 28. Such a separate collection device can also be supplied with excess fluid directly from the second fluid-outlet device outlets 24. Furthermore, it is provided, as explained in greater detail further below, to return excess fluid to the fluid inlet 8 via the second fluid-outlet device outlets 24 (with or without excess fluid container 26). Supplementary or optionally, excess fluid can (also) be transferred to a separate experimental set-up (e.g. a further downstream sample exposition arrangement) for further use.

The excess fluid container 26 can be releasably connected to the fluid-outlet device outlets 24. This enables, for example, removal of the excess fluid container 26 together with the fluid collected therein. The excess fluid container 26 can also have the same effect as the exhaust of, for example, a motor vehicle, namely reduce fluctuations in the fluid flow arising during supply of fluid to the sample containers 6.

Fluctuations in the fluid flow can occur, in particular, when a negative pressure is generated in the sample containers 6 for supplying fluid thereto in order to draw in, for example, a specific amount of fluid per unit of time.

The fluid outlet devices 16 are connected to the distribution device outlets 32 of the distribution device 12 via their fluid-outlet device inlets 30. The distribution device outlets 32 are arranged in a row just as the sample containers 6 and the fluid outlet devices 16. The arrangement of the distribution device outlets 32 in a row enables the use of at least one row of linearly arranged sample containers 6. In known arrangements, circularly arranged sample containers are often used which may make it difficult to extend the arrangement by additional sample containers. In a linear sample container arrangement, as provided by the present invention, this is not the case. Moreover, the space requirements are greater in a circular arrangement. By means of a linear arrangement, for example, six sample containers can each be charged with different fluids.

Furthermore, it is provided to configure the distribution device 12 such that the guideways (e.g. channels) in the distribution device 12, beginning at the distribution device inlet 34 up to the distribution device outlets 32, at least substantiallycorrespond to each other. This can be achieved, for example, by dimensioning the fluid guideways in the distribution device 12 equally (e.g. equal in length, equal in diameter). One aspect of the present disclosure is to configure such equal fluid guideways in the distribution device 12 in a manner which enables a linear arrangement of the distribution device outlets 32 in a row. This described in greater detail further below.

Figure 2:
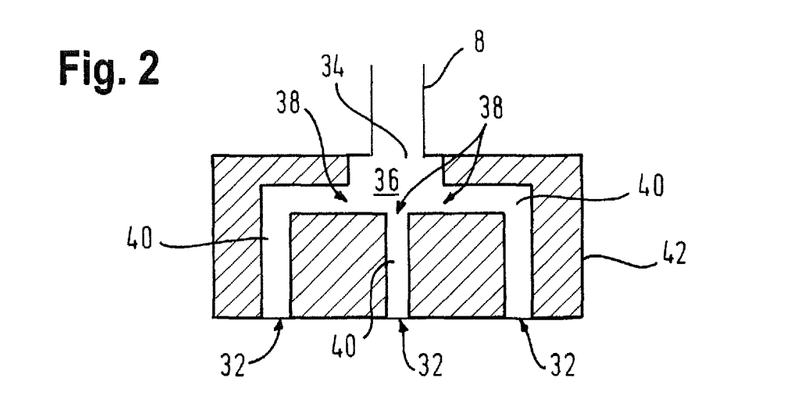
FIG. 2 shows schematic cross-sectional views of an embodiment of a distribution apparatus.

FIG. 2 schematically illustrates the structure of a distribution device 12. Fluid received via the distribution device inlet 34 is supplied to a distribution chamber 36. The distribution chamber 36 comprises outlet openings 38 leading to fluid guideways 40 which, in turn, terminate in the distribution device outlets 32. The number of the outlet openings 38, fluid guideways 40 and distribution device outlets 32, respectively, may depend upon how often fluid is to be divided. In this connection, it is provided to divide the fluid for each sample container 6 and to accordingly use a number of outlet openings 38, fluid guideways 40 and distribution device outlets 32, respectively, which corresponds to the number of sample containers 6. It is possible to divide the fluid more than once for one or more sample containers 6 and to accordingly use more than two outlet openings 38, fluid guideways 40 and distribution device outlets 32 for these sample containers 6 in each case. In such cases, when more than two distribution device outlets 32 are provided for one sample container 6, it is possible to connect each of them with a fluid outlet device 16 of its own, or to assign a common fluid outlet device 16 to a number of or all distribution device outlets associated with a sample container 6.

The fluid guideways 40 are illustrated as angled channels differing in length in the embodiment of FIG. 2. In further embodiments, the fluid guideways 40 are all substantially equal in length and/or equal in cross section. Furthermore, the fluid guideways 40 can be curved so that, in particular, uniform fluid flows free of turbulence, etc. are obtained.

In the embodiment of FIG. 2, the distribution device inlet 34, the distribution chamber 36, the outlet openings 38 thereof as well as the fluid guideways 40 and the distribution device outlets 32 are formed within one body 42. The body 42 can be integrally formed, as shown, and be made of, for example, inter alia plastic material, metal, ceramics and/or glass. The body 42 is shown as an integral body, however, may also be composed of multiple pieces, as explained further below. In the following, it is firstly referred to the body 42. However, explanations in this respect also apply to correspondingly differently configured components, such as e.g. a first body of the distribution device described further below.

Figure 3:
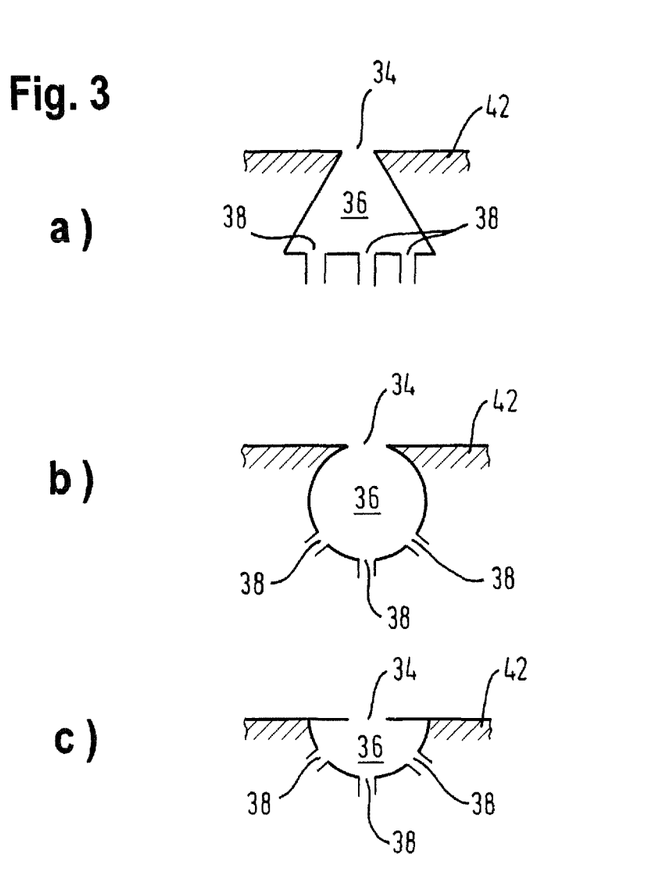
FIG. 3 shows schematic illustrations of embodiments of distribution chambers for distribution apparatuses.

FIG. 3 shows a number of embodiments of distribution chambers 36 of the distribution device 12. The pyramid or frustum-shaped, spherical or hemispherical distribution chambers 36 illustrated in FIGS. 3 (*a*), (*b*), and (*c*) are formed within the body 42.

The exemplary distribution chambers 36 shown in FIGS. 3 (*d*), (*e*), (*f*), and (*g*) comprise a first distribution chamber part 44 formed within the body 42 and a second distribution chamber part 46 defined by a cover 48. The cover 48 is releasably connected to the body 42, for example, by means of screw and/or plug-in/snap-on/snap-fit connections. Such embodiments may facilitate access to the distribution chambers 36, for example, for cleaning the same. In such embodiments, different distribution chambers 36 may be obtained by combining a type of distribution chamber part 44 with various covers 48 without further modifications to the general arrangement. For example, the distribution chamber parts 44 of FIGS. 3 (*d*) and (*e*), which correspond to each other, can be combined with the cover 48 of FIG. 3 (*d*) to obtain a spherical distribution chamber 36, and with the cover 48 of FIG. 3 (*e*) to obtain a hemispherical distribution chamber 36.

Furthermore, such embodiments enable a combination of different first and second distribution chamber parts. For example, the cover 48 of FIG. 3 (*d*) can be combined with the first distribution chamber part 44 of FIG. 3 (*f*) or (*g*).

As illustrated in FIG. 3 (*h*), a means 50 having an effect on flow, such as e.g. a deflector surface, swirl body and/or turbulence element, can be arranged within the distribution chamber 36 irrespective of the shape thereof.

FIGS. 3 (*i*) and (*j*) show a further variant of a distribution chamber 36. In FIG. 3 (*i*) a view into the distribution chamber 36 in the direction of flow is illustrated, while FIG. 3 (*j*) shows a cross-sectional view. In the shown embodiment, three outlet openings 38 leading to fluid guideways 40 are shown. A fluid guiding recess 64 is assigned to each of the outlet openings 38. The fluid guiding recesses 64 are deepest where they coincide with or adjoin the respective outlet opening 38 and level out towards the center. The fluid guiding recesses 64 can improve the distribution of fluid to the outlet openings 38 and thus to the fluid guideways 40 and finally to the sample containers 6.

Figure 4:
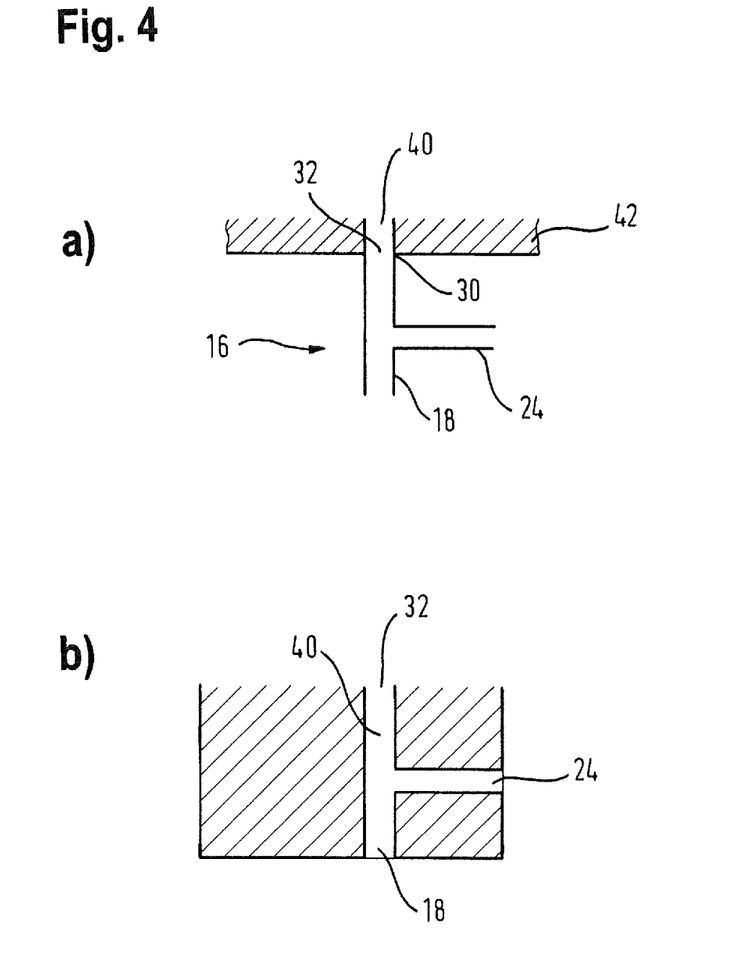
FIG. 4 shows schematic cross-sectional views of embodiments of fluid outlet devices.

FIG. 4 illustrates embodiments of the configuration of fluid outlet devices 16. In the variant shown in FIG. 4 (*a*), the fluid outlet device 16 is arranged outside the body 42, while in the variant shown in FIG. 4 (*b*), the fluid outlet device 16 is arranged within the body 42.

Figure 5:
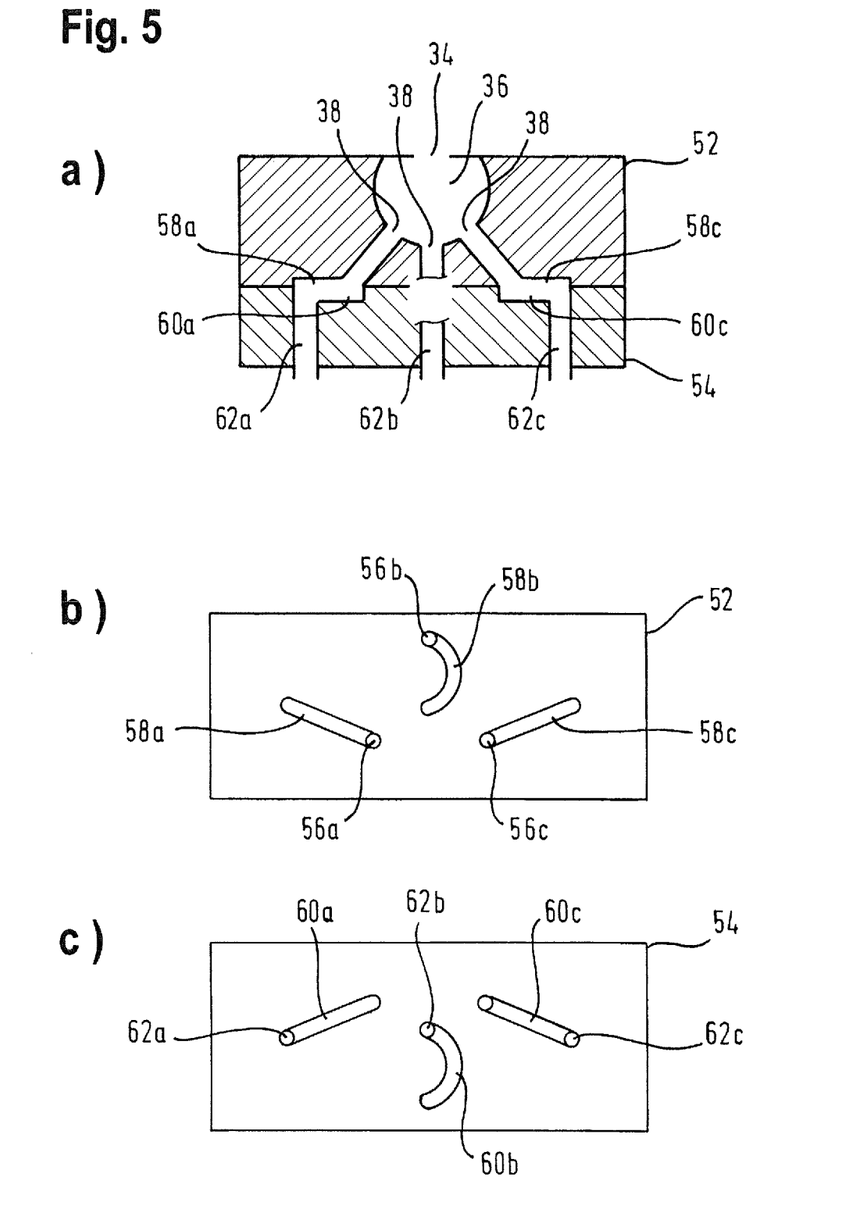
FIG. 5 shows schematic cross-sectional views of an embodiment of a triple distribution apparatus.

FIG. 5 shows an embodiment of the distribution device 12 having three exemplarily chosen fluid guideways 40, which are intended to supply one sample container each. The body 42 of the distribution device 12 of this embodiment comprises a first body 52 and a second body 54. The bodies 52 and 54 can be integrally formed, for example, depending on the manufacturing method. In such cases, the bodies 52 and 54 may thus also be referred to as body parts of the body 42. Furthermore, the bodies 52 and 54 may each, in turn, be made of one, two or multiple pieces, for example, also depending on the manufacturing method. The first body 52 and the second body 54 can be made of, for example, inter alia plastic material, metal, ceramics and/or glass, wherein the bodies 52 and 54 may also differ in structure and/or can be connected to each other by means of screw and/or plug-in/snap-on/snap-fit connections. The bodies 52, 54 and 42 may also all be integrally formed.

In the variant of FIG. 5, the fluid guideways 40 are equal in dimension and, in particular, equal in length and substantially equal in diameter in all places. In order to achieve this, in connection with the fact that the distribution device outlets 32 are arranged in a row, it is proceeded as follows. Beginning at the outlet openings 38 of the distribution chamber 36, the fluid guideways 40 initially extend substantially in a straight line, for example, in the form of bores. These regions of the fluid guideways 40 terminate at and open into, respectively, locations designated by 56*a*, 56*b* and 56*c* in FIG. 5 (*a*), which are also indicated in FIG. 5 (*b*), and transition into recesses 58*a*, 58*b* and 58*c* within the first body 52 at said locations.

As illustrated in FIG. 5 (*b*), recesses 58*a*, 58*b* and 58*c* are formed in the side of the first body 52 which is the bottom side in FIG. 5 (*a*). The recesses 58*a*, 58*b* and 58*c* are shaped such that, when the first body 52 and the second body 54 are connected to each other, they each form a part of the corresponding fluid guideway 40 together with recesses 60*a*, 60*b* and 60*c* formed in the second body and described below.

As illustrated in FIG. 5 (*c*), the recesses 60*a*, 60*b* and 60*c* are formed in the side of the second body 54 which is the top side in FIG. 5(*a*). The recesses 60*a*, 60*b* and 60*c* terminate at passages 62*a*, 62*b* and 62*c*, when viewed in the direction of flow, which extend through the second body 54 towards the fluid-outlet device inlets 30, from where fluid may reach the distribution device outlets 32.

By means of the regions of the left and right fluid guideways 40 formed by recesses 58a/60a and 58c/60c extending obliquely to the horizontal plane of representation and by the arc-shaped course of the region of the central fluid guideway 40 formed by recesses 58b/60b it is achieved, on the one hand, that the fluid guideways 40 are substantially equal in dimension, equal in length and substantially equal in cross section in all places and, on the other hand, that the distribution device outlets 32 are arranged in a row. The latter, in connection with a corresponding linear arrangement of the fluid outlet devices 16 and the first fluid-outlet device outlets 18 thereof, enables supply of sample containers also arranged linearly in a row.

Figure 6:
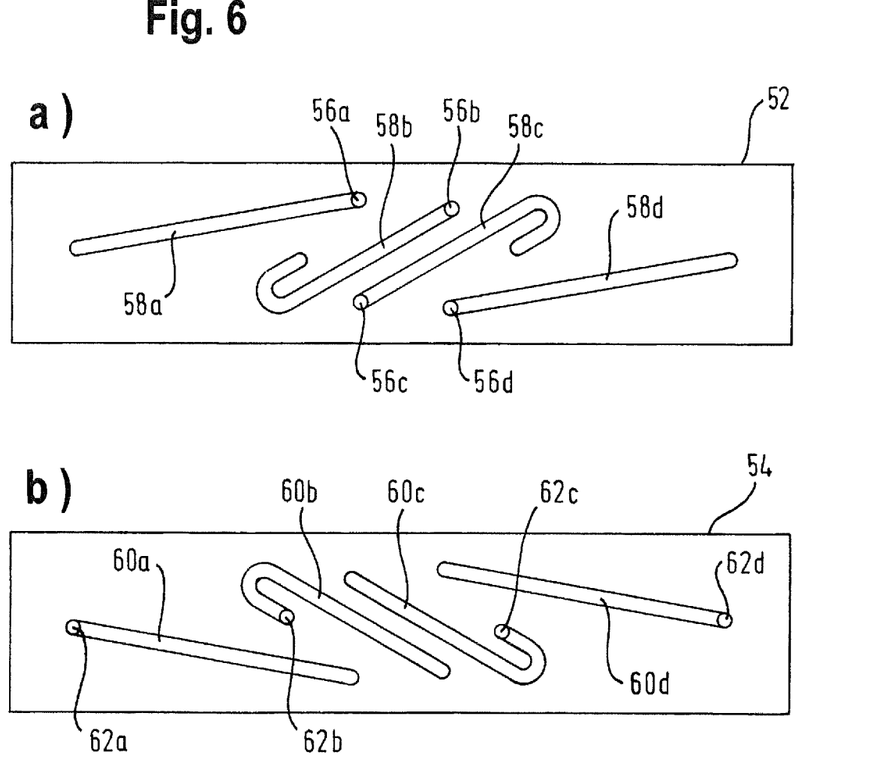
FIG. 6 shows schematic cross-sectional views of an embodiment of a quadruple distribution apparatus.

FIG. 6 shows an embodiment of the distribution device 12 having four exemplarily chosen fluid guideways 40 which are intended to supply one sample container each. As far as not stated otherwise in the following, the above explanations, in particular with respect to FIG. 5, also apply to FIGS. 6.

The body 42 of the distribution device 12 of this embodiment comprises a first body 52 and a second body 54. The bodies 52 and 54 can be integrally formed, for example, depending on the manufacturing method. In such cases, the bodies 52 and 54 may thus also be referred to as body parts of the body 42. Furthermore, the bodies 52 and 54 may each, in turn, be made of one, two or multiple pieces, for example, also depending on the manufacturing method. The bodies 52, 54 and 42 may also all be integrally formed.

The first body 52 and the second body 54 can be made of, for example, inter alia plastic material, metal, ceramics and/or glass, wherein the bodies 52 and 54 may also differ in structure and/or can be connected to each other by means of screw and/or plug-in/snap-on/snap-fit connections.

In the variant of FIG. 6, the fluid guideways 40 are equal in dimension and, in particular, equal in length and substantially equal in diameter in all places. In order to achieve this, in connection with the fact that the distribution device outlets 32 are arranged in a row, it is proceeded as follows. Beginning at the outlet openings 38 of the distribution chamber 36, the fluid guideways 40 initially extend substantially in a straight line, for example, in the form of bores. These regions of the fluid guideways 40 terminate at and open into, respectively, locations designated by 56a, 56b, 56c and 56d in FIG. 6 (b) and transition into recesses 58a, 58b, 58c and 58d within the first body 52 at said locations.

As illustrated in FIG. 6 (a), recesses 58a, 58b, 58c and 58d are formed in the bottom side of the first body 52. The recesses 58a, 58b, 58c and 58d are shaped such that, when the first body 52 and the second body 54 are connected to each other, they each form a part of the corresponding fluid guideway 40 together with recesses 60a, 60b, 60c and 60d formed in the second body and described below.

As illustrated in FIG. 6 (b), the recesses 60a, 60b, 60c and 60d are formed in the top side of the second body 54. The recesses 60a, 60b, 60c and 60d terminate at passages 62a, 62b, 62c and 62d, when viewed in the direction of flow, which extend through the second body 54 towards the fluid-outlet device inlets 30, from where fluid may reach the distribution device outlets 32.

By means of the arc-shaped courses of the regions of the fluid guideways 40 formed by recesses 58a/60a, 58a/60b, 58c/60c and 58d/60d it is achieved, on the one hand, that the fluid guideways 40 are substantially equal in dimension, equal in length and substantially equal in cross section in all places and, on the other hand, that the distribution device outlets 32 are arranged in a row. The latter, in connection with a corresponding linear arrangement of the fluid outlet devices 16 and the first fluid-outlet device outlets 18 thereof, enables supply of sample containers also arranged linearly in a row.

Figure 7:
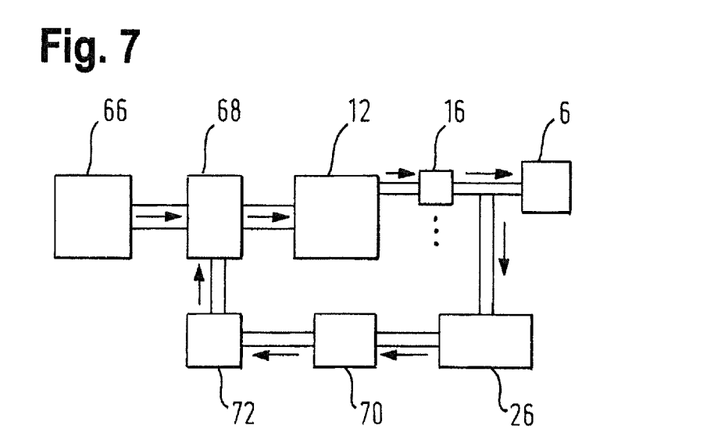
FIG. 7 shows a schematic illustration of a sample exposition arrangement with optional fluid feedback.
Figure 8:
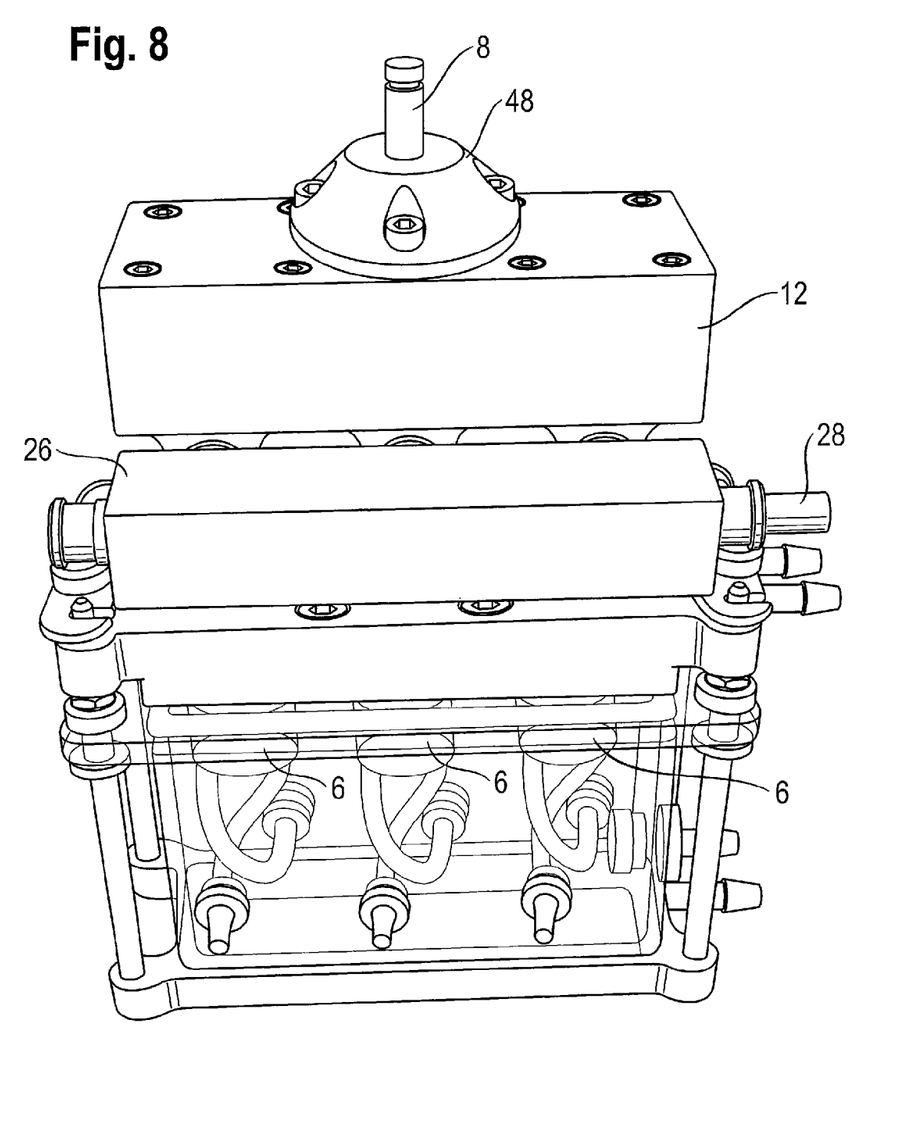
FIG. 8 shows an illustration of a sample exposition arrangement including a distribution apparatus.
Figure 9:
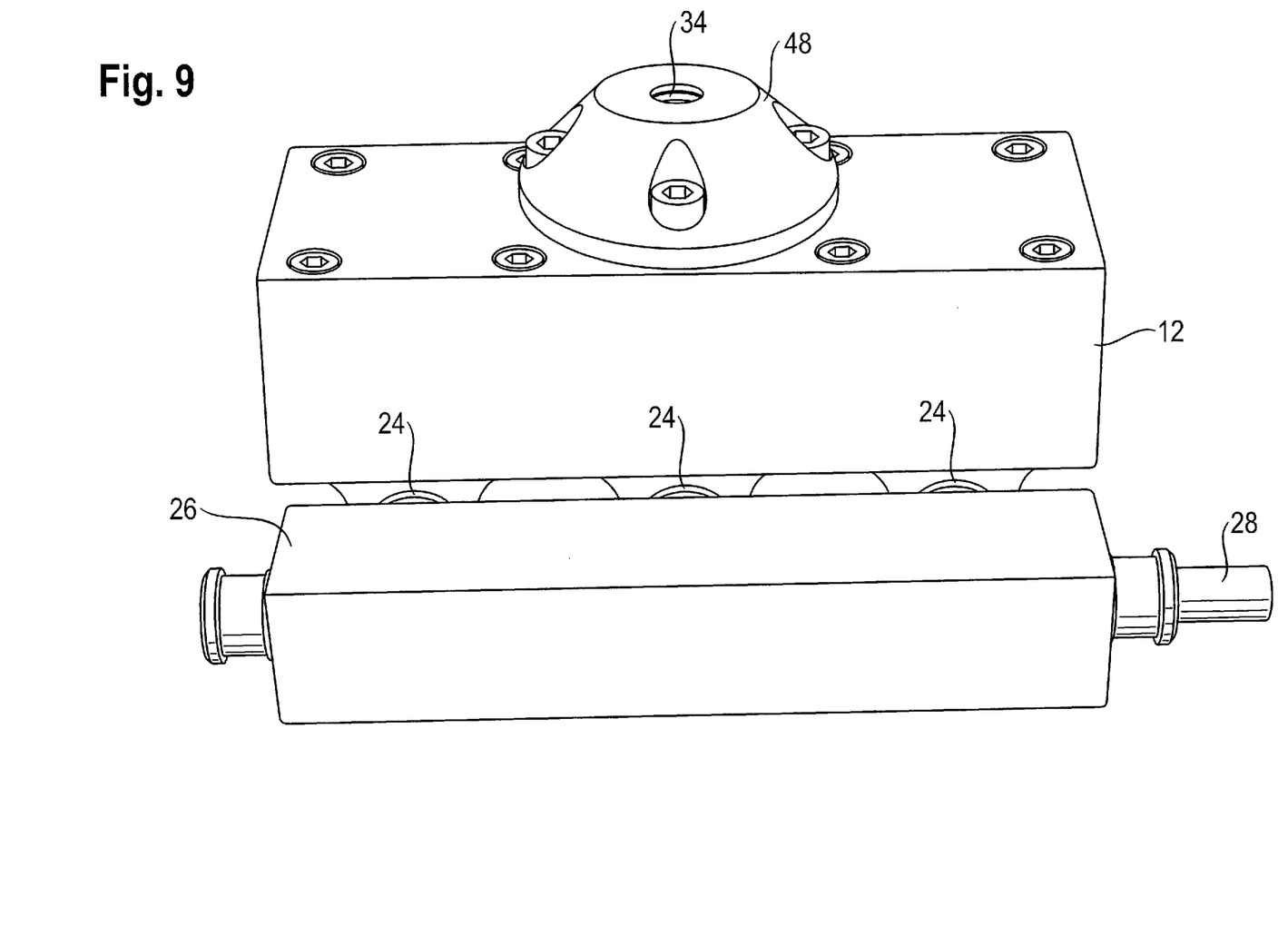
FIG. 9 shows a perspective view of the distribution apparatus of FIG. 8.
Figure 10:
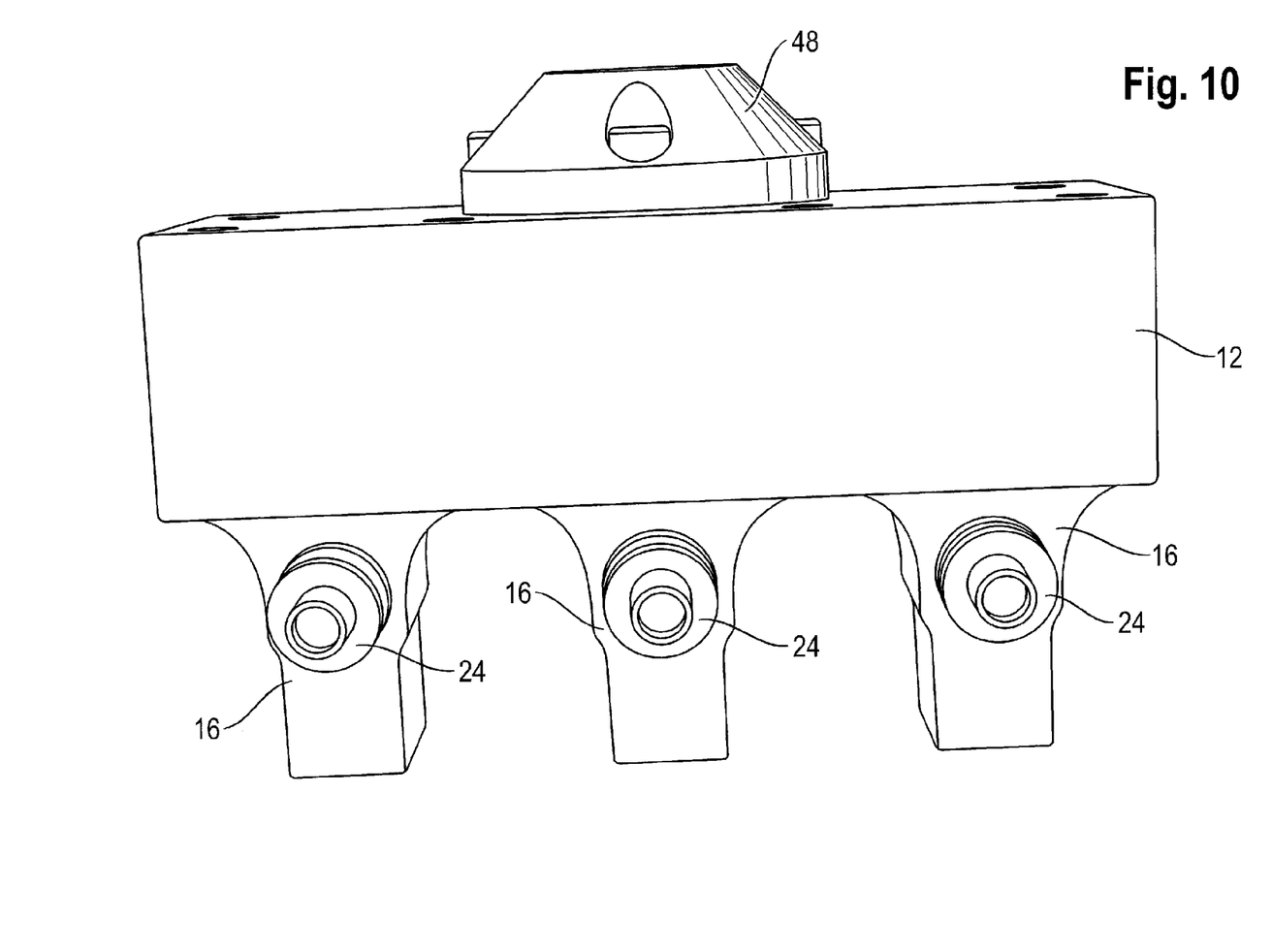
FIG. 10 shows an illustration of the distribution apparatus of FIG. 8 without an excess fluid container.
Figure 11:
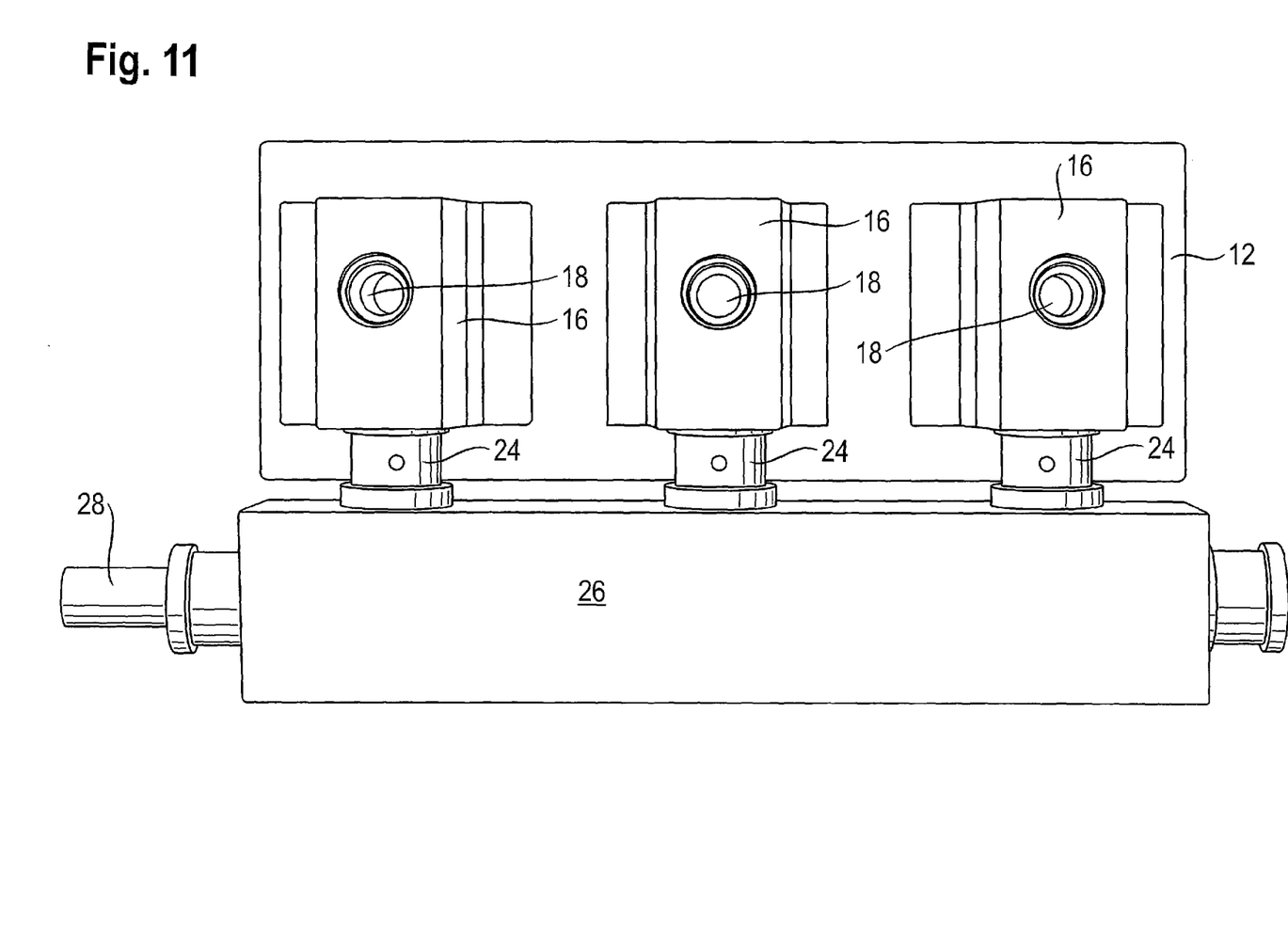
FIG. 11 shows an illustration of the discharge side of the distribution apparatus of FIG. 8.
Figure 12:
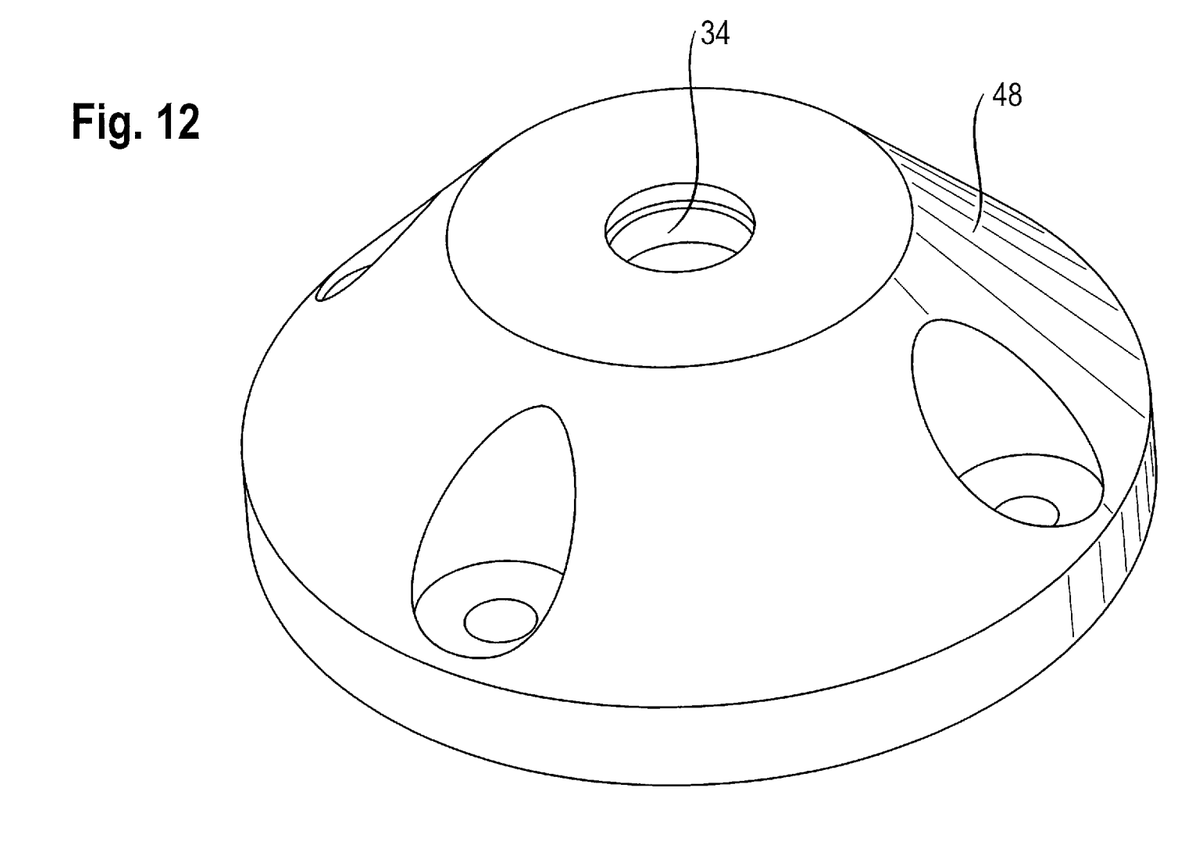
FIG. 12 shows an illustration of a cover of the distribution device of the distribution apparatus of FIG. 8.

FIG. 7 illustrates an embodiment of a sample exposition arrangement including a distribution device 12, in which excess fluid can be returned and reused. Fluid provided by a fluid source 66 is supplied to a distribution device 12 via a fluid supply selection device 68 described in greater detail further below and is supplied to fluid outlet devices 16 from said distribution device in a distributed manner. Fluid required for sample exposition is supplied from the fluid outlet devices 16 to the sample containers 6. Fluid not required for sample exposition is directly or indirectly returned to the fluid supply selection device 68 as excess fluid.

By means of the fluid supply selection device 68 it is selectively possible to supply fluid from the fluid source 66 or returned fluid as well as mixtures thereof to the distribution device 12, from where the above described cycle can be repeated (a number of times). The fluid supply selection device 68 may comprise, for example, a two or three-way valve.

An excess fluid container 26, a volume compensation device 70 and/or a feeding device 72 can each be optionally arranged between the second fluid-outlet device outlets 24 and the selection device 68.

The above explanations with respect to the excess fluid container 26 apply accordingly here. The volume compensation device 70 serves the purpose of compensating the amount of fluid which is required for sample exposition and is supplied to the sample containers 6. For example, a container having a variable volume (comparable to a gas bag or a container with variable receiving volume) can be used as the volume compensation device 70.

The feeding device 70 serves the purpose of producing, maintaining or only just assisting a fluid flow to supply a sufficient fluid flow to the distribution apparatus 2 on the inlet side.

The invention claimed is:

1. A distribution apparatus for at least two sample containers and a fluid source for fluid to be supplied to the sample containers, the distribution apparatus comprising:
   a distribution device including
      a distribution device inlet for supplying fluid to the distribution device,
      a plurality of distribution device outlets, including one distribution device outlet for each sample container, and
      a distribution chamber between the distribution device inlet and the distribution device outlets, and
   a plurality of fluid outlet devices, including at least one fluid outlet device per distribution device outlet, wherein each fluid outlet device comprises
      one fluid-outlet device inlet, each of which is in fluid communication with the corresponding distribution device outlet,
      a first fluid-outlet device outlet for discharging fluid into the corresponding sample container, and
      a second fluid-outlet device outlet for discharging excess fluid.

2. The distribution apparatus according to claim 1, wherein the distribution device comprises at least one fluid guideway between the distribution chamber and the distribution device outlets.

3. The distribution apparatus according to claim 1, wherein the distribution chamber is substantially spherical or emispherical in shape.

4. The distribution apparatus according to claim 1, wherein a device having an effect on flow is arranged within the distribution chamber.

5. The distribution apparatus according to claim 1, wherein the distribution device comprises at least one fluid guideway, and wherein a fluid guiding recess for each fluid guideway is formed in an inner surface of the distribution chamber.

6. The distribution apparatus according to claim 1, wherein the distribution device comprises a removable cover defining at least one part of the distribution chamber.

7. The distribution apparatus according to claim 1, wherein the distribution chamber is connected to at least one of the distribution device outlets by a fluid guideway, and the distribution chamber and at least one of the fluid guideways are formed at least partially within a first body.

8. The distribution apparatus according to claim 7, wherein the first body and a second body each comprise complementary recesses forming the fluid guideway.

9. The distribution apparatus according to claim 1, wherein the distribution chamber is connected to at least one of the distribution device outlets by a fluid guideway, and wherein at least one of the fluid guideways is at least partially formed within a body.

10. The distribution apparatus according to claim 1, wherein the distribution device comprises at least one fluid guideway connecting the distribution chamber to the distribution device outlets, and wherein at least one of the fluid guideway is curved.

11. The distribution apparatus according to claim 1, wherein the fluid-outlet device outlets are in fluid communication with an excess fluid container for discharging excess fluid.

12. The distribution apparatus according to claim 11, wherein the excess fluid container comprises an outlet for discharging fluid present therein.

13. The distribution apparatus according to claim 1, further comprising a fluid supply selection device which is in fluid communication with the second fluid-outlet device outlets and the distribution device inlet and which is adapted to supply fluid from the fluid source and fluid from the second fluid-outlet device outlets to the distribution device inlet.

14. The distribution apparatus according to claim 1, further comprising a fluid volume compensation device which is in fluid communication with the second fluid-outlet device outlets.

15. A sample exposition arrangement comprising a distribution apparatus according to claim 1.

16. The sample exposition arrangement according to claim 15, comprising at least two sample containers and a fluid source for fluid to be supplied to the sample containers.

* * * * *